(12) United States Patent
Wolfe et al.

(10) Patent No.: US 11,273,138 B2
(45) Date of Patent: Mar. 15, 2022

(54) USE OF AMINO ACID SUPPLEMENTATION FOR IMPROVED MUSCLE PROTEIN SYNTHESIS

(71) Applicant: BioVentures, LLC, Little Rock, AR (US)

(72) Inventors: Robert R. Wolfe, Little Rock, AR (US); Arny Ferrando, Little Rock, AR (US)

(73) Assignee: BioVentures, LLC, Little Rock, AR (US)

( * ) Notice: Subject to any disclaimer, the term of this patent is extended or adjusted under 35 U.S.C. 154(b) by 0 days.

(21) Appl. No.: 16/761,175

(22) PCT Filed: Nov. 2, 2018

(86) PCT No.: PCT/US2018/058937
§ 371 (c)(1),
(2) Date: May 1, 2020

(87) PCT Pub. No.: WO2019/090061
PCT Pub. Date: May 9, 2019

(65) Prior Publication Data
US 2020/0253908 A1    Aug. 13, 2020

Related U.S. Application Data

(60) Provisional application No. 62/580,861, filed on Nov. 2, 2017.

(51) Int. Cl.
| | | |
|---|---|---|
| A61K 31/198 | (2006.01) | |
| A23L 33/175 | (2016.01) | |
| A61K 31/405 | (2006.01) | |
| A61K 31/4172 | (2006.01) | |

(52) U.S. Cl.
CPC .......... *A61K 31/198* (2013.01); *A23L 33/175* (2016.08); *A61K 31/405* (2013.01); *A61K 31/4172* (2013.01)

(58) Field of Classification Search
CPC .............. A61K 2300/00; A61K 31/198; A61K 31/405; A61K 31/4172; A23L 33/17; A23L 33/175
See application file for complete search history.

(56) References Cited

U.S. PATENT DOCUMENTS

| | | | |
|---|---|---|---|
| 4,851,226 A | 7/1989 | Julian et al. | |
| 5,075,114 A | 12/1991 | Roche | |
| 5,817,329 A | 10/1998 | Gardiner | |
| 5,876,759 A | 3/1999 | Gowan | |
| 7,288,570 B2 | 10/2007 | Verlaan et al. | |
| 7,790,688 B2 | 9/2010 | Wolfe et al. | |
| 8,703,725 B2 | 4/2014 | Troup et al. | |
| 8,846,759 B2 | 9/2014 | Luiking et al. | |
| 9,364,463 B2 | 6/2016 | Ferrando et al. | |
| 9,597,367 B2 | 3/2017 | Wolfe et al. | |
| 10,022,358 B2 | 7/2018 | Wolfe et al. | |
| 2003/0162241 A1 | 8/2003 | Pittner et al. | |
| 2008/0268038 A1 | 10/2008 | Wolfe | |
| 2009/0297689 A1 | 12/2009 | Edens | |
| 2010/0267831 A1* | 10/2010 | Kobayashi | A61P 3/02 514/561 |
| 2012/0245331 A1 | 9/2012 | Takakura et al. | |
| 2013/0203658 A1 | 8/2013 | Luiking et al. | |
| 2013/0203701 A1 | 8/2013 | Leighton | |
| 2013/0210780 A1 | 8/2013 | Jourdan et al. | |
| 2014/0315788 A1* | 10/2014 | Wolfe | A23L 33/175 514/2.7 |
| 2014/0343112 A1 | 11/2014 | Ferrando et al. | |
| 2014/0357576 A1 | 12/2014 | Breuille et al. | |
| 2016/0219910 A1 | 8/2016 | Silver et al. | |
| 2017/0143679 A1 | 5/2017 | Wolfe et al. | |

FOREIGN PATENT DOCUMENTS

| | | |
|---|---|---|
| EP | 0399341 A1 | 11/1990 |
| WO | 1991009524 A1 | 7/1991 |
| WO | 2013075095 A1 | 5/2013 |
| WO | 2017106687 A1 | 6/2017 |
| WO | 2019090061 A1 | 5/2019 |

OTHER PUBLICATIONS

Bohe, J. et al., "Human muscle protein synthesis is modulated by extracellular, not intramuscular amino acid availability: a dose-response study," J. Physiol., 2003, pp. 315-324, vol. 552.1, The Physiological Society.
Extended European Search Report dated Jul. 21, 2021 from related European Patent Application No. 18874200.1; 8 pgs.
Ferrando, A. et al., "EAA supplementation to increase nitrogen intake improves muscle function during bed rest in the elderly," Clin. Nutrit., 2010, pp. 18-23, vol. 29, No. 1, Elsevier Ltd.
Fiatarone, M. et al., "Exercise Training and Nutritional Supplementation for Physical Frailty in Very Elderly People," NEJM, Jun. 23, 1994, pp. 1769-1775, vol. 330, No. 25, Massachusetts Medical Society.
Gapeyeva, H. et al., "Quadriceps femoris muscle voluntary isometric force production and relaxation characteristics before and 6 months after unilateral total knee arthroplasty in women," Knee Surg. Sports Traumatol. Arthrosc., 2007, pp. 202-211, vol. 15, No. 2, Springer-Verlag.
Garlick, P. et al., "Critical Assessment of Methods Used to Measure Protein Synthesis in Human Subjects," Yale J. Biol. Med., 1997, pp. 65-76, vol. 70.

(Continued)

*Primary Examiner* — Savitha M Rao
(74) *Attorney, Agent, or Firm* — Polsinelli PC

(57) ABSTRACT

The present invention encompasses an amino acid composition for stimulating muscle protein synthesis. Further, the present disclosure relates generally to the use of an anabolic amino acid composition for the stimulation of muscle protein synthesis. In particular, disclosed are compositions and methods of using the same for the prevention and/or treatment of a loss of any one of muscle mass, muscle strength, muscle function, and physical function, or any combination thereof, in a mammal, especially an adult mammal. Also provided are kits comprising a composition for the stimulation of muscle protein synthesis and, in certain embodiments, instructions for administration.

13 Claims, No Drawings

(56) References Cited

OTHER PUBLICATIONS

Interational Search Report and Written Opinion dated Feb. 7, 2013 from related Patent Application No. PCT/US2012/065842, 11 pgs.
International Search Report and Written Opinion dated Jan. 17, 2019 from related Patent Application No. PCT/US2018/058937; 11 pgs.
Katsanos, C. et al., "A high proportion of leucine is required for optimal stimulation of the rate of muscle protein synthesis by essential amino adds in the elderly," Am. J. Physiol. Endrocrinol. Metab., 2006, pp. E381-E387, vol. 291, American Physiological Society.
Kim, J. et al., "Total-body skeletal muscle mass: estimation by a new dual-energy X-ray absorptiometry methods," Am. J. Clin. Nutr., 2002, pp. 378-383, vol. 76.
Notice of Allowance dated Mar. 16, 2016 from related U.S. Appl. No. 14/359,213; 8 pgs.
Notice of Allowance dated Nov. 10, 2016 from related U.S. Appl. No. 14/256,323; 5 pgs.
Notice of Allowance dated Mar. 20, 2018 from related U.S. Appl. No. 15/424,311; 6 pgs.
Office Action dated Oct. 29, 2015 from related U.S. Appl. No. 14/359,213; 15 pgs.
Office Action dated Jun. 21, 2016 from related U.S. Appl. No. 14/256,323; 9 pgs.
Office Action dated Dec. 5, 2017 from related U.S. Appl. No. 15/424,311; 4 pgs.
University of Arkansas for Medical Sciences, "Essential Amino Add Supplementation for Recovery from Hip Surgery: Supporting clinical data," Jul. 20, 2010, (retrieved Jan. 2, 2013), 3 pgs., Available on the internet: <URL:http://www.ibridgenetwork.org/uams/essential-amino-acid-supplementation-for-recovery-from-hip-su>.
Unver, B. et al., "Ability to Rise Independently From a Chair During 6-Month Follow-up After Unilateral and Bilateral Total Knee Replacement," J. Rehabil. Med., 2005, pp. 385-387, vol. 37, No. 6, Taylor & Francis.
Wolfe, R., "The role of dietary protein in optimizing muscle mass, function and health outcomes in older individuals," Br. J. Nutr., 2012, pp. S88-S93, vol. 108.
Office Action dated Nov. 2, 2021 from related Singaporean Patent Application No. 11202003370V; 8 pgs.

* cited by examiner

USE OF AMINO ACID SUPPLEMENTATION FOR IMPROVED MUSCLE PROTEIN SYNTHESIS

CROSS REFERENCE TO RELATED APPLICATIONS

This application claims the benefit of International Application No. PCT/US2018/058937, filed Nov. 02, 2018, which claims the benefit of U.S. Provisional Application 62/580,861, filed Nov. 02, 2017, the disclosures of which are hereby incorporated by reference in their entirety.

GOVERNMENTAL RIGHTS

This invention was made with government support under AR052293 awarded by the National Institute of Health. The government has certain rights in the invention.

FIELD OF THE INVENTION

The present disclosure relates generally to the use of an anabolic amino acid composition for the stimulation of muscle protein synthesis. In particular, disclosed are compositions and methods of using the same for the prevention and/or treatment of a loss of any one of muscle mass, muscle strength, muscle function, and physical function, or any combination thereof, in a mammal, especially an adult mammal.

BACKGROUND

Large dosages of dietary protein are required to stimulate muscle protein synthesis. The anabolic effects of nutrition are principally driven by the transfer and incorporation of amino acids captured from dietary protein sources, into skeletal muscle proteins. The purpose of this is to compensate for muscle protein that is lost in fasted (postabsorptive) periods due to, for example, amino acid oxidation and/or carbon donation for liver gluconeogenesis. However, as humans age the body's ability to digest protein becomes less efficient. Muscle mass loss starts from the age of 30 years at a rate of 3-8% per decade and accelerates from 60 years of age. This loss reaches up to 35-40% in elderly over 70, and hence, sarcopenia is especially prominent in elderly. Consequently, age associated progressive loss of muscle mass increases the risks of injury and disability.

Thus, there is a need for a nutritional supplement to expedite rate of muscle protein synthesis to a greater extent that would be expected from consumption of dietary protein.

SUMMARY

Among various aspects of the present disclosure are methods and compositions for stimulating muscle protein synthesis. In general, the present disclosure provides a nutritional composition comprising effective amounts of amino acids which stimulate muscle protein synthesis in a subject relative to a subject not administered the composition.

One aspect of the present disclosure is directed to the provision of a composition comprising histidine, isoleucine, leucine, lysine, methionine, phenylalanine, threonine, valine, tryptophan, and arginine. In one aspect, the present disclosure provides a composition comprising the following concentrations of amino acids in terms of w/w %: about 1 to 2% of histidine, about 9 to 11% of isoleucine, about 35 to 38% of leucine, about 14 to 17% of lysine, about 2 to 4% of methionine, about 5 to 7% of phenylalanine, about 8 to 9% of threonine, about 9 to 11% of valine, about 0.005 to 0.8% of tryptophan, and about 8 to 11% of arginine.

In another aspect, muscle protein synthesis improves approximately 50% with a minimum dose of 3.6 grams. In yet another aspect, the composition comprises the following concentrations of amino acids in terms of w/w %: 1.5% of histidine, 9.7% of isoleucine, 36.4% of leucine, 15.2% of lysine, 3% of methionine, 6.1% of phenylalanine, 8.5% of threonine, 10% of valine, 0.6% of tryptophan, and 9% of arginine.

A further aspect of the present disclosure is directed to a method of administering a nutritional composition comprising amino acids at a 12 g dose once a day, at a 3.6 g dose three times a day, at a 3.6 g dose one time a day, at a 3.6 g dose two times a day, at a 6.7 g dose once a day, at a 6.7 g dose two times a day, or at a 6.7 g dose three times a day.

An additional aspect provides a composition comprising the following amino acids; histidine, isoleucine, leucine, lysine, methionine, phenylalanine, threonine, valine, tryptophan, and arginine that stimulates muscle protein synthesis more than 50% at dosages less than 12 grams with or without exercise.

In yet another aspect, the present disclosure provides a composition and method of using the same for stimulating muscle protein synthesis using a dosage of less than 12 grams. In some embodiments, the composition comprises the following concentrations of amino acids in terms of w/w %: about 1 to 2% of histidine, about 9 to 11% of isoleucine, about 35 to 38% of leucine, about 14 to 17% of lysine, about 2 to 4% of methionine, about 5 to 7% of phenylalanine, about 8 to 9% of threonine, about 9 to 11% of valine, about 0.005 to 0.8% of tryptophan, and about 8 to 11% of arginine.

While multiple embodiments are disclosed, still other embodiments of the present invention will become apparent to those skilled in the art from the following detailed description, which shows and describes illustrative embodiments of the invention. Accordingly, the detailed description is to be regarded as illustrative in nature and not restrictive.

DETAILED DESCRIPTION

The disclosure provides, generally, methods and compositions comprising a specific amino acid formulation capable of stimulating the rate of muscle protein synthesis. Applicants have found the compositions as described herein surprisingly stimulate muscle protein synthesis in a highly efficient manner. In particular, the compositions as disclosed herein stimulate the production of more muscle protein than the total weight of the components ingested. According to the invention, it was discovered that a formulation containing free essential amino acids (EAA) and arginine in specific amounts, is well suited for stimulation of muscle protein synthesis. In particular, it has been discovered that nutritional compositions comprising a mixture of essential amino acids and arginine, including substantial amounts of leucine, effectively stimulate muscle protein synthesis. Advantageously, the formulation was found to be effective in adults where stimulation of muscle protein synthesis is less efficient. The muscle protein synthesis is improved relative subjects that did not receive said amino acid composition and occurs with or without exercise.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules of the compound are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Various aspects of the invention are described in further detail in the following sections.

(I) Compositions

Provided herein are anabolic amino acid compositions composition useful for the stimulation of muscle protein synthesis. In some embodiments, the composition may comprise the essential amino acids histidine, isoleucine, leucine, lysine, methionine, phenylalanine, threonine, valine, and tryptophan. In preferred embodiments, the composition may comprise the amino acid arginine in addition to the essential amino acids histidine, isoleucine, leucine, lysine, methionine, phenylalanine, threonine, valine, and tryptophan.

In general, the amino acids may be L-amino acids, D-amino acids or mixtures thereof. In preferred embodiments, the amino acids are L-amino acids. Those of skill in the art will appreciate that the amino acids of the composition may be free amino acids or amino acids salts. The amino acid composition of the invention may also be in the form of intact protein or peptide, provided that the protein or peptide comprises the amino acids of the invention in the correct concentrations relative to each other. In preferred embodiments, the amino acids of the invention are free amino acids or amino acids salts. If not obtained commercially, individual amino acids may be produced by methods well known in the art, including chemical synthesis or use of recombinant microorganisms.

The amino acids may be the canonical amino acids histidine, isoleucine, leucine, lysine, methionine, phenylalanine, threonine, valine, tryptophan, and arginine, or non-canonical amino acid derivatives (e.g. a precursor to an amino acid). Non-limiting examples of non-canonical amino acids that may be used in the invention include L-lysine acetate, derivatives of L-tyrosine, ornithine, keto acid analogs, hydrochloride salt (L-cysteine HCL.H$_2$O), and N-acetyl derivatives of the various amino acids. In preferred embodiments, the amino acids used in the compositions and solutions of the present invention may be in free form or salt form.

In one aspect, an amino acid composition of the disclosure comprises one or more essential amino acids. An essential amino acid (EAA) is an amino acid that cannot be synthesized de novo by a subject, and therefore must be supplied in its diet. The amino acids regarded as essential for humans are phenylalanine, valine, threonine, tryptophan, methionine, leucine, isoleucine, lysine, and histidine. In some embodiments, a combination of EEAs comprises phenylalanine, valine, threonine, tryptophan, methionine, leucine, isoleucine, lysine, and histidine. In preferred embodiments, the amino acid composition also comprises at least one conditionally essential amino acid.

The amino acids arginine, cysteine, glycine, glutamine, proline, serine and tyrosine are considered conditionally essential, meaning they are not normally required in the diet, but must be supplied exogenously to specific populations that do not synthesize them in adequate amounts. For example, the body produces sufficient arginine to satisfy metabolic requirements under normal conditions. Therefore, arginine supplementation is not necessary to stimulate muscle protein synthesis for many subjects. However, in certain clinical circumstances, including in elderly with heart failure, endogenous arginine production is inadequate to meet all demands. For such a population, it is advantageous for combinations of the invention to comprise arginine, or a precursor of the amino acid arginine. The term "amino acid precursor" refers to a metabolic precursor of an amino acid. For example, serine is a metabolic precursor of cysteine and glycine; and 3-phosphoglycerate is a metabolic precursor of serine and, therefore, of cysteine and glycine too. As a second example, citrulline is a metabolic precursor of arginine. The metabolic pathways that synthesize amino acids are well known in the art, and a skilled artisan may refer to these to identify metabolic precursors of other amino acids. In some embodiments, a combination of the invention comprises phenylalanine, valine, threonine, tryptophan, methionine, leucine, isoleucine, lysine, histidine, and at least one conditionally essential amino acid. For example, the combination may comprise 1, 2, 3, 4, 5, 6, 7, 8, 9, or 10 conditionally essential amino acids. In other embodiments, a combination of the invention comprises phenylalanine, valine, threonine, tryptophan, methionine, leucine, isoleucine, lysine, histidine, and at least one conditionally essential amino acid precursor. For example, the combination may comprise 1, 2, 3, 4, 5, 6, 7, 8, 9, or 10 conditionally essential amino acid precursors. In still other embodiments, a combination of the invention comprises phenylalanine, valine, threonine, tryptophan, methionine, leucine, isoleucine, lysine, histidine, at least one non-essential amino acid and at least one conditionally essential amino acid precursor.

In some embodiments, the composition may comprise the following concentrations of histidine in terms of w/w %: about 1% to about 2%, about 1.1% to about 2%, about 1.2% to about 2%, about 1.3% to about 2%, about 1.4% to about 2%, about 1.5% to about 2%, about 1.6% to about 2%, about 1.7% to about 2%, about of 1.8% to about 2%, about 1.9% to about 2%, about 1% to about 1.9%, about 1% to about 1.8%, about 1% to about 1.7%, about 1% to about 1.6%, about 1% to about 1.5%, about 1% to about 1.4%, about 1% to about 1.3%, about 1% to about 1.2%, or about 1% to about 1.1% of histidine.

In some embodiments, the composition may comprise the following concentrations of isoleucine in terms of w/w %: about 9% to about 11%, about 9.1% to about 11%, about 9.2% to about 11%, about 9.3% to about 11%, about 9.4% to about 11%, about 9.4% to about 11%, about 9.4% to about 11%, about 9.5% to about 11%, about 9.6% to about 11%, about 9.7% to about 11%, about 9.8% to about 11%, about 9.9% to about 11%, about 10% to about 11%, about 10.1% to about 11%, about 10.2% to about 11%, about 10.3% to about 11%, about 10.4% to about 11%, about 10.5% to about 11%, about 10.6% to about 11%, about 10.7% to about 11%, about 10.8% to about 11%, about 10.9% to about 11%, about 9% to about 10.9%, about 9% to about 10.8%, about 9% to about 10.7%, about 9% to about 10.6%, about 9% to about 10.5%, about 9% to about 10.4%, about 9% to about 10.3%, about 9% to about 10.2%, about 9% to about 10.1%, about 9% to about 10%, about 9% to about 9.9%, about 9% to about 9.8%, about 9% to about 9.7%, about 9% to about 9.6%, about 9% to about 9.5%, about 9% to about 9.4%, about 9% to about 9.3%, about 9% to about 9.2%, or about 9% to about 9.1% of isoleucine.

In some embodiments, the composition may comprise the following concentrations of leucine in terms of w/w %: about 35% to about 38%, about 35.2% to about 38%, about 35.4% to about 38%, about 35.6% to about 38%, about 35.8% to about 38%, about 36% to about 38%, about 36.2% to about 38%, about 36.4% to about 38%, about 36.6% to about 38%, about 36.8% to about 38%, about 37% to about 38%, about 37.2% to about 38%, about 37.4% to about 38%, about 37.6% to about 38%, about 37.8% to about 38%, about 35% to about 37.8%, about 35% to about 37.6%, about 35% to about 37.4%, about 35% to about 37.2%, about 35% to about 37%, about 35% to about 36.8%, about 35% to about 36.6%, about 35% to about 36.4%, about 35% to about 36.2%, about 35% to about 36%, about 35% to about 35.8%, about 35% to about 35.6%, about 35% to about 35.4%, or about 35% to about 35.2% of leucine.

In some embodiments, the composition may comprise the following concentrations of lysine in terms of w/w %: about 14% to about 17%, about 14.2% to about 17%, about 14.4% to about 17%, about 14.6% to about 17%, about 14.8% to about 17%, about 15% to about 17%, about 15.2% to about 17%, about 15.4% to about 17%, about 15.6% to about 17%, about 15.8% to about 17%, about 16% to about 17%, about 16.2% to about 17%, about 16.4% to about 17%, about 16.6% to about 17%, about 16.8% to about 17%, about 14% to about 16.8%, about 14% to about 16.6%, about 14% to about 16.4%, about 14% to about 16.2%, about 14% to about 16%, about 14% to about 15.8%, about 14% to about 15.6%, about 14% to about 15.4%, or about 14% to about 15.2% of lysine.

In some embodiments, the composition may comprise the following concentrations of methionine in terms of w/w %: about 2% to about 4%, about 2.1% to about 4%, about 2.2% to about 4%, about 2.3% to about 4%, about 2.4% to about 4%, about 2.5% to about 4%, about 2.6% to about 4%, about 2.7% to about 4%, about 2.8% to about 4%, about 2.9% to about 4%, about 3% to about 4%, about 3.1% to about 4%, about 3.2% to about 4%, about 3.3% to about 4%, about 3.4% to about 4%, about 3.5% to about 4%, about 3.6% to about 4%, about 3.7% to about 4%, about 3.8% to about 4%, about 3.9% to about 4%, about 2% to about 3.9%, about 2% to about 3.8%, about 2% to about 3.7%, about 2% to about 3.6%, about 2% to about 3.5%, about 2% to about 3.4%, about 2% to about 3.3%, about 2% to about 3.2%, about 2% to about 3.1%, about 2% to about 3%, about 2% to about 2.9%, about 2% to about 2.8%, about 2% to about 2.7%, about 2% to about 2.6%, about 2% to about 2.5%, about 2% to about 2.4%, about 2% to about 2.3%, about 2% to about 2.2%, or about 2% to about 2.1% of methionine.

In some embodiments, the composition may comprise the following concentrations of phenylalanine in terms of w/w %: about 5% to about 7%, about 5.1% to about 7%, about 5.2% to about 7%, about 5.3% to about 7%, about 5.4% to about 7%, about 5.5% to about 7%, about 5.6% to about 7%, about 5.7% to about 7%, about 5.8% to about 7%, about 5.9% to about 7%, about 6% to about 7%, about 6.1% to about 7%, about 6.2% to about 7%, about 6.3% to about 7%, about 6.4% to about 7%, about 6.5% to about 7%, about 6.6% to about 7%, about 6.7% to about 7%, about 6.8% to about 7%, about 6.9% to about 7%, about 5% to about 6.9%, about 5% to about 6.8%, about 5% to about 6.7%, about 5% to about 6.6%, about 5% to about 6.5%, about 5% to about 6.4%, about 5% to about 6.3%, about 5% to about 6.2%, about 5% to about 6.1%, about 5% to about 6%, about 5% to about 5.9%, about 5% to about 5.8%, about 5% to about 5.7%, about 5% to about 5.6%, about 5% to about 5.5%, about 5% to about 5.4%, about 5% to about 5.3%, about 5% to about 5.2%, or about 5% to about 5.1% of phenylalanine In some embodiments, the composition may comprise the following concentrations of threonine in terms of w/w %: about 8% to about 9%, about 8.1% to about 9%, about 8.2% to about 9%, about 8.3% to about 9%, about 8.4% to about 9%, about 8.5% to about 9%, about 8.6% to about 9%, about 8.7% to about 9%, about 8.8% to about 9%, about 8.9% to about 9%, about 8% to about 8.9%, about 8% to about 8.8%, about 8% to about 8.7%, about 8% to about 8.6%, about 8% to about 8.5%, about 8% to about 8.4%, about 8% to about 8.3%, about 8% to about 8.2%, or about 8% to about 8.1% of threonine In some embodiments, the composition may comprise the following concentrations of valine in terms of w/w %: about 9% to about 11%, about 9.1% to about 11%, about 9.2% to about 11%, about 9.3% to about 11%, about 9.4% to about 11%, about 9.4% to about 11%, about 9.4% to about 11%, about 9.5% to about 11%, about 9.6% to about 11%, about 9.7% to about 11%, about 9.8% to about 11%, about 9.9% to about 11%, about 10% to about 11%, about 10.1% to about 11%, about 10.2% to about 11%, about 10.3% to about 11%, about 10.4% to about 11%, about 10.5% to about 11%, about 10.6% to about 11%, about 10.7% to about 11%, about 10.8% to about 11%, about 10.9% to about 11%, about 9% to about 10.9%, about 9% to about 10.8%, about 9% to about 10.7%, about 9% to about 10.6%, about 9% to about 10.5%, about 9% to about 10.4%, about 9% to about 10.3%, about 9% to about 10.2%, about 9% to about 10.1%, about 9% to about 10%, about 9% to about 9.9%, about 9% to about 9.8%, about 9% to about 9.7%, about 9% to about 9.6%, about 9% to about 9.5%, about 9% to about 9.4%, about 9% to about 9.3%, about 9% to about 9.2%, or about 9% to about 9.1% of valine.

In some embodiments, the composition may comprise the following concentrations of tryptophan in terms of w/w %: about 0.005% to about 0.8%, about 0.006% to about 0.8%, about 0.007% to about 0.8%, about 0.008% to about 0.8%, about 0.009% to about 0.8%, about 0.01% to about 0.8%, about 0.02% to about 0.8%, about 0.03% to about 0.8%, about 0.04% to about 0.8%, about 0.05% to about 0.8%, about 0.06% to about 0.8%, about 0.07% to about 0.8%, about 0.08% to about 0.8%, about 0.09% to about 0.8%, about 0.1% to about 0.8%, about 0.2% to about 0.8%, about 0.3% to about 0.8%, about 0.4% to about 0.8%, about 0.5% to about 0.8%, about 0.6% to about 0.8%, about 0.7% to about 0.8%, about 0.005% to about 0.7%, about 0.005% to about 0.6%, about 0.005% to about 0.5%, about 0.005% to about 0.4%, about 0.005% to about 0.3%, about 0.005% to about 0.2%, about 0.005% to about 0.1%, about 0.005% to about 0.09%, about 0.005% to about 0.08%, about 0.005% to about 0.07%, about 0.005% to about 0.06%, about 0.005% to about 0.05%, about 0.005% to about 0.04%, about 0.005% to about 0.03%, about 0.005% to about 0.02%, about 0.005% to about 0.01%, about 0.005% to about 0.009%, about 0.005% to about 0.008%, about 0.005% to about 0.007%, or about 0.005% to about 0.006% of tryptophan In some embodiments, the composition may comprise the following concentrations of arginine in terms of w/w %: about 8% to about 11%, about 8.1% to about 11%, about 8.2% to about 11%, about 8.3% to about 11%, about 8.4% to about 11%, about 8.5% to about 11%, about 8.6% to about 11%, about 8.7% to about 11%, about 8.8% to about 11%, about 8.9% to about 11%, about 9% to about 11%, about 9.1% to about 11%, about 9.2% to about 11%, about 9.3% to about 11%, about 9.4% to about 11%, about 9.4% to about 11%, about 9.4% to about 11%, about 9.5% to about 11%, about 9.6% to about 11%, about 9.7% to about 11%, about 9.8% to about 11%, about 9.9% to about 11%, about 10% to about 11%, about 10.1% to about 11%, about10.2% to about 11%, about 10.3% to about 11%, about 10.4% to about 11%, about 10.5% to about 11%, about 10.6% to about 11%, about 10.7% to about 11%, about 10.8% to about 11%, about 10.9% to about 11%, about 8% to about 10.8%, about 8% to about 10.7%, about 8% to about 10.6%, about 8% to about 10.5%, about 8% to about 10.4%, about 8% to about 10.3%, about 8% to about 10.2%, about 8% to about 10.1%, about 8% to about 10%, about 8% to about 9.9%, about 8% to about 9.8%, about 8% to about 9.7%, about 8% to about 9.6%, about 8% to about 9.5%, about 8% to about 9.4%, about 8% to about 9.3%, about 8% to about 9.2%, about 8% to about 9.1%, about 8% to about 9%, about 8% to about 8.9%, about 8% to about 8.8%, about 8% to about 8.7%, about 8% to about 8.6%, about 8% to about 8.5%, about 8% to about 8.4%, about 8% to about 8.3%, about 8% to about 8.2%, or about 8% to about 8.1% of arginine In some embodiments, the composition may comprise the following concentrations of amino acids in terms of w/w %: about 1% to about 2% of histidine, about 9% to about 11% of isoleucine, about 35% to about 38% of leucine, about 14% to about 17% of lysine, about 2% to about 4% of methionine, about 5% to about 7% of phenylalanine, about 8% to about 9% of threonine, about 9% to about 11% of valine, about 0.005% to about 0.8% of tryptophan, and about 8% to about 11% of arginine. In exemplary embodiments, the composition may comprise, consist essentially, or consist of 1.5% of histidine, 9.7% of isoleucine, 36.4% of leucine, 15.2% of lysine, 3% of methionine, 6.1% of phenylalanine, 8.5% of threonine, 10% of valine, 0.6% of tryptophan, and 9% of arginine.

In another aspect, combinations of the invention may further comprise one or more additional nutrients. The term "nutrient", as used herein, refers to prebiotics, vitamins, carbohydrates, fiber, fatty acids, sulfates, minerals, antioxidants, and other food ingredients used in subject's metabolism which are taken in from its environment. Suitable vitamins may include, but are not limited to: vitamin B1, vitamin B2, vitamin B3, vitamin B5, vitamin B6, vitamin B9, vitamin B12, lipoic acid, vitamin A, biotin, vitamin K, vitamin C, vitamin D, and vitamin E. Suitable minerals may include, but are not limited to compounds containing: iron, copper, magnesium, manganese, molybdenum, nickel, and zinc. Suitable enzyme cofactors may include, but are not limited to: adenosine triphosphate (ATP), S-adenosyl methionine (SAM), coenzyme B, coenzyme M, coenzyme Q, glutathione, heme, methanofuran, and nucleotide sugars. Suitable lipids may include, but are not limited to, fatty acids, glycerolipids, glycerophospholipids, sphingolipids, sterol lipids, prenol lipids, saccharolipids and polyketides. Non-limiting examples of fatty acids include myristoleic acid, palm itoleic acid, sapienic acid, oleic acid, elaidic acid, vaccenic acid, linoleic acid, linoelaidic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, cerotic acid, hexadecatrienoic acid, alpha-linolenic acid, stearidonic acid, eicosatetraenoic acid, eicosapentaenoic acid, heneicosapentaenoic acid, docosapentaenoic acid, clupanodonic acid, docasehaenoic acid, tetracosapentaenoic acid, and tetracosahexaenoic acid. Additional non-limiting examples of nutrients may include Thiamin, Riboflavin, Niacin, Folate, Pantothenic acid, Calcium, Phosphorus, Magnesium, Manganese, Iron, Zinc, Copper, Selenium, Sodium, Potassium, betacarotene, retinol, alphatocopherol, betatocopherol, gammatocopherol, deltatocopherol, alphatoctrienol, betatoctrienol, gammatocotrienol, deltatocotrienol, apo-8-carotenal, trans-lycopene, cis-lycopene, trans-beta-carotene, and cis-beta-carotene, caffeine. In some embodiments, combinations of the invention further comprise one nutrient. In other embodiments, combinations of the invention further comprise at least one nutrient. For example, a combination of the invention may comprise 1, 2, 3, 4, 5, 6, 7, 8, 9, 10 or more nutrients. In still other embodiments, combinations of the invention further comprise two or more nutrients. In preferred embodiments, combinations of the invention further comprise at least one nutrient selected from the group consisting of omega-3 fatty acid and biotin. In other preferred embodiments, combinations of the invention further comprise two nutrients selected from the group consisting of omega-3 fatty acid and biotin. The overall contribution of the one or more nutrients to the total weight of the combination is substantially less than the contribution of the plurality of amino acids. Generally, the one or more nutrients comprise no more than about 10% by weight, preferably no more than about 5% by weight, more preferably no more than about 3% by weight of the combination. In preferred embodiments, the one or more nutrient is biotin. In other preferred embodiments, the one or more nutrient is one or more omega-3 fatty acid. In other preferred embodiments, the one or more nutrient is biotin and one or more omega-3 fatty acid.

(II) Formulations

In each of the above embodiments, amino acids and nutrients (when present) may be formulated for animal or human use. In some embodiments, each amino acid and nutrient (when present) is formulated separately. In other embodiments, two or more amino acids and nutrients (when present) are formulated together. In still other embodiments, all the amino acids and nutrients comprising a combination of the invention are formulated together. The one or more formulations may then be processed into one or more dosage forms that can be administered together, sequentially, or over a period of time (for example, over 1 minute, 10 minutes, 30 minutes, 1 hour, 3 hours, 6 hours, 9 hours, 12 hours, 18 hours, 24 hours, or more). Administration can be performed using standard effective techniques, including oral, parenteral (e.g. intravenous, intraperitoneal, subcutaneous, intramuscular), buccal, sublingual, or suppository administration. The term orally, as used herein, refers to any form of administration by mouth, including addition of a composition to animal feed or other food product. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Methods of preparing compositions for animal or human use are well known in the art. For instance, a composition may be generally formulated as a liquid composition, a solid composition or a semi-solid composition. Liquid compositions include, but are not limited to, aqueous suspensions, solutions, emulsions, elixirs, or syrups. Liquid composition will typically include a solvent carrier selected from a polar solvent, a non-polar solvent, or a combination of both. The choice of solvent will be influenced by the properties of the components of the composition. For example, if the components are water-soluble, a polar solvent may be used. Alternatively, if the components of the composition are lipid-soluble, a non-polar solvent may be used. Suitable polar and non-polar solvents are known in the art. Semi-solid compositions include douches, suppositories, creams, and topicals. Dry compositions include, but are not limited to, reconstitutable powders, chewable tablets, quick dissolve tablets, effervescent tablets, multi-layer tablets, bi-layer tablets, capsules, soft gelatin capsules, hard gelatin capsules, caplets, lozenges, chewable lozenges, beads, powders, granules, particles, microparticles, and dispersible granules. Formulations may include a combination of the invention along with an excipient. Non-limiting examples of excipients include binders, diluents (fillers), disintegrants, effervescent disintegration agents, preservatives (antioxidants), flavor-modifying agents, lubricants and glidants, dispersants, coloring agents, pH modifiers, chelating agents, antimicrobial agents, release-controlling polymers, and combinations of any of these agents.

Non-limiting examples of binders suitable for the formulations of various embodiments include starches, pregelatinized starches, gelatin, polyvinylpyrolidone, cellulose, methylcellulose, sodium carboxymethylcellulose, ethylcellulose, polyacrylam ides, polyvinyloxoazolidone, polyvinylalcohols, C12-C18 fatty acid alcohols, polyethylene glycol, polyols, saccharides, oligosaccharides, polypeptides, oligopeptides, and combinations thereof. The polypeptide may be any arrangement of amino acids ranging from about 100 to about 300,000 Daltons. In one embodiment, the binder may be introduced into the mixture to be granulated in a solid form including but not limited to a crystal, a particle, a powder, or any other finely divided solid form known in the art. In another embodiment, the binder may be dissolved or suspended in a solvent and sprayed onto the mixture in a granulation device as a binder fluid during granulation.

Non-limiting examples of diluents (also referred to as "fillers" or "thinners") include carbohydrates, inorganic compounds, and biocompatible polymers, such as polyvinylpirrolydone (PVP). Other non-limiting examples of diluents include dibasic calcium sulfate, tribasic calcium sulfate, starch, calcium carbonate, magnesium carbonate, microcrystalline cellulose, dibasic calcium phosphate, tribasic calcium phosphate, magnesium carbonate, magnesium oxide, calcium silicate, talc, modified starches, saccharides such as sucrose, dextrose, lactose, microcrystalline cellulose, fructose, xylitol, and sorbitol, polyhydric alcohols; starches; pre-manufactured direct compression diluents; and mixtures of any of the foregoing.

Disintegrents may be effervescent or non-effervescent. Non-limiting examples of non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Suitable effervescent disintegrants include but are not limited to sodium bicarbonate in combination with citric acid, and sodium bicarbonate in combination with tartaric acid.

Non-limiting examples of preservatives include, but are not limited to, ascorbic acid and its salts, ascorbyl palm itate, ascorbyl stearate, anoxomer, N-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), eucalyptus extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytryrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palm ityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., Ionox 100), 2,4-(tris-3',5'-bi-tert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, wheat germ oil, zeaxanthin, or combinations thereof. In an exemplary embodiment, the preservatives is an antioxidant, such as a-tocopherol or ascorbate, and antimicrobials, such as parabens, chlorobutanol or phenol.

Suitable flavor-modifying agents include flavorants, taste-masking agents, sweeteners, and the like. Flavorants include, but are not limited to, synthetic flavor oils and flavoring aromatics and/or natural oils, extracts from plants, leaves, flowers, fruits, and combinations thereof. Other non-limiting examples of flavors include cinnamon oils, oil of wintergreen, peppermint oils, clover oil, hay oil, anise oil, eucalyptus, vanilla, citrus oils such as lemon oil, orange oil, grape and grapefruit oil, fruit essences including apple, peach, pear, strawberry, raspberry, cherry, plum, pineapple, and apricot.

Taste-masking agents include but are not limited to cellulose hydroxypropyl ethers (HPC) such as Klucel®, Nisswo HPC and PrimaFlo HP22; low-substituted hydroxypropyl ethers (L-HPC); cellulose hydroxypropyl methyl ethers (HPMC) such as Seppifilm-LC, Pharmacoat®, Metolose SR, Opadry YS, PrimaFlo, MP3295A, Benecel MP824, and Benecel MP843; methylcellulose polymers such as Methocel® and Metolose®; Ethylcelluloses (EC) and mixtures thereof such as E461, Ethocel®, Aqualon®-EC, Surelease; Polyvinyl alcohol (PVA) such as Opadry AMB; hydroxyethylcelluloses such as Natrosol®; carboxymethylcelluloses and salts of carboxymethylcelluloses (CMC) such as Aualon®-CMC; polyvinyl alcohol and polyethylene glycol copolymers such as Kollicoat IR®; monoglycerides (Myverol), triglycerides (KLX), polyethylene glycols, modified food starch, acrylic polymers and mixtures of acrylic polymers with cellulose ethers such as Eudragit® EPO, Eudragit® RD100, and Eudragit® E100; cellulose acetate phthalate; sepifilms such as mixtures of HPMC and stearic acid, cyclodextrins, and mixtures of these materials. In other embodiments, additional taste-masking agents contemplated are those described in U.S. Pat. Nos. 4,851,226, 5,075,114, and 5,876,759, each of which is hereby incorporated by reference in its entirety.

Non-limiting examples of sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia rebaudiana (Stevioside); chloro derivatives of sucrose such as sucralose; sugar alcohols such as sorbitol, mannitol, sylitol, hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

Lubricants may be utilized to lubricate ingredients that form a composition of the invention. As a glidant, the lubricant facilitates removal of solid dosage forms during the manufacturing process. Non-limiting examples of lubricants and glidants include magnesium stearate, calcium stearate, zinc stearate, hydrogenated vegetable oils, sterotex, polyoxyethylene monostearate, talc, polyethylene glycol, sodium benzoate, sodium lauryl sulfate, magnesium lauryl sulfate, and light mineral oil. The composition will generally comprise from about 0.01% to about 10% by weight of a lubricant. In some embodiments, the composition will comprise from about 0.1% to about 5% by weight of a lubricant. In a further embodiment, the composition will comprise from about 0.5% to about 2% by weight of a lubricant.

Dispersants may include but are not limited to starch, alginic acid, polyvinylpyrrolidones, guar gum, kaolin, bentonite, purified wood cellulose, sodium starch glycolate, isoamorphous silicate, and microcrystalline cellulose as high hydrophilic-lipophilic balance (HLB) emulsifier surfactants.

Depending upon the embodiment, it may be desirable to include a coloring agent. Suitable color additives include but are not limited to food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in various embodiments.

Non-limiting examples of pH modifiers include citric acid, acetic acid, tartaric acid, malic acid, fumaric acid, lactic acid, phosphoric acid, sorbic acid, benzoic acid, sodium carbonate and sodium bicarbonate.

A chelating agent may be included as an excipient to immobilize oxidative groups, including but not limited to metal ions, in order to inhibit the oxidative degradation of the morphinan by these oxidative groups. Non-limiting examples of chelating agents include lysine, methionine, glycine, gluconate, polysaccharides, glutamate, aspartate, and disodium ethylenediaminetetraacetate ($Na^2EDTA$).

An antimicrobial agent may be included as an excipient to minimize the degradation of the compound according to this disclosure by microbial agents, including but not limited to bacteria and fungi. Non-limiting examples of antimicrobials include parabens, chlorobutanol, phenol, calcium propionate, sodium nitrate, sodium nitrite, $Na^2EDTA$, and sulfites including but not limited to sulfur dioxide, sodium bisulfite, and potassium hydrogen sulfite.

Release-controlling polymers may be included in the various embodiments of the solid dosage compositions incorporating compounds according to this disclosure. In one embodiment, the release-controlling polymers may be used as a tablet coating. In other embodiments, including but not limited to bilayer tablets, a release-controlling polymer may be mixed with the granules and other excipients prior to the formation of a tablet by a known process including but not limited to compression in a tablet mold. Suitable release-controlling polymers include but are not limited to hydrophilic polymers and hydrophobic polymers.

Suitable hydrophilic release-controlling polymers include, but are not limited to, cellulose acetate, cellulose diacetate, cellulose triacetate, cellulose ethers, hydroxyethyl cellulose, hydroxypropyl cellulose, hydroxypropyl methylcellulose, microcrystalline cellulose, nitrocellulose, cross-linked starch, agar, casein, chitin, collagen, gelatin, maltose, mannitol, maltodextrin, pectin, pullulan, sorbitol, xylitol, polysaccharides, ammonia alginate, sodium alginate, calcium alginate, potassium alginate, propylene glycol alginate, alginate sodium carmellose, calcium carmellose, carrageenan, fucoidan, furcellaran, arabicgum, carrageensgum, ghaftigum, guargum, karayagum, locust beangum, okragum, tragacanthgum, scleroglucangum, xanthangum, hypnea, laminaran, acrylic polymers, acrylate polymers, carboxyvinyl polymers, copolymers of maleic anhydride and styrene, copolymers of maleic anhydride and ethylene, copolymers of maleic anhydride propylene or copolymers of maleic anhydride isobutylene), crosslinked polyvinyl alcohol and poly N-vinyl-2-pyrrolidone, diesters of polyglucan, polyacrylam ides, polyacrylic acid, polyam ides, polyethylene glycols, polyethylene oxides, poly(hydroxyalkyl methacrylate), polyvinyl acetate, polyvinyl alcohol, polyvinyl chloride, polystyrenes, polyvinylpyrrolidone, anionic and cationic hydrogels, and combinations thereof.

The amino acid compositions as disclosed herein can also include compositions that can be created as a powder that can be added to food items, as a baked good (e.g., as cookies and brownies), and as a concentrate. The concentrate can be added to water or another ingestible liquid to create a nutritional beverage. The nutritional supplement is typically contained within a one-serving or multiple serving container such as a package, box, carton, wrapper, bottle or can. Where the nutritional supplement is prepared in the form of a concentrate that can be added to and mixed with a beverage, a bottle or can be used for packaging the concentrate. The nutritional supplement can also include water.

(a) Amino Acid Dose

As will be appreciated by one of skill in the art, the dose of the amino acid composition of the invention can and will vary depending on the body weight, sex, age and/or medical condition of the subject, the intensity of the physical exercise by the subject, the method of administration. Non-limiting examples of species may include a human, a companion animal, a lab animal, a zoo animal or an agricultural animal. Routine experimentation may readily establish the required dosage. Typical amino acid doses for oral administration may be about 7 g per dose. In some embodiments, an amino acid dose of about 3, 4, 5, 10, or 12 g of the amino acid composition may be administered. In other embodiments, an amino acid dose of about 3, 4, 5, 6, 7, 8, 9, 10, 11, or 12 g of the amino acid composition may be administered. In an exemplary embodiment, the amino acid dose may be about 7 g per dose.

Administering multiple doses of the amino acid composition per day may also be used as needed to provide the desired stimulation of muscle protein synthesis. For instance, one, two, three, four, or more doses of the amino acid composition may be administered per day. In a preferred embodiment, one dose of the amino acid composition may be administered per day. In another preferred embodiment, two doses of the amino acid composition may be administered per day. In yet another preferred embodiment, three doses of the amino acid composition may be administered per day.

The timing and duration of administration of the composition of the invention can and will vary. For instance, when the composition is administered to stimulate muscle protein synthesis with or without exercise, the composition may be administered without an exercise routine, before starting an exercise routine, during the exercise routine or after an exercise routine. Alternatively, when the composition is administered to improve muscle protein synthesis in a subject prone to muscle issues such as an older human subject, the composition may be administered on a regular basis.

In an exemplary embodiment, when the subject is human, three doses of 3 g per dose of the amino acid composition may be administered per day. In another exemplary embodiment, two doses of 7 g per dose of the amino acid composition may be administered per day. In yet another exemplary embodiment, a single dose of 7 g per dose of the amino acid composition may be administered per day.

(b) Administration

The composition of the invention may be administered as intravenous, intramuscular, subcutaneous injection or parenteral routes. In some embodiments, the composition may be formulated for administration by injection (e.g., intraperitoneally, intravenously, subcutaneously, intramuscularly, etc.). Accordingly, these compositions are preferably combined with pharmaceutically acceptable vehicles such as saline, Ringer's solution, dextrose solution, and the like.

The amino acid composition of the invention may comprise a pharmaceutical carrier (or excipient). Such a carrier may be any solvent or solid material for encapsulation that is non-toxic. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995).

For parenteral administration (including subcutaneous, intradermal, intravenous, intramuscular, and intraperitoneal), the composition may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

In a preferred embodiment, the amino acid composition of the invention may be administered orally. Non-limiting examples of oral formulations that may be used to administer the amino acid composition of the invention may be a nutritional formulation, a medical food, a medical beverage, in the form of a complete meal, part of a meal, as a food additive as a powder for dissolution, in the form of a pharmaceutical formulation such as in the form of a tablet, pill, sachet or capsule or by tube feeding such as by means of nasogastric, nasoduodenal, esophagostomy, gastrostomy, or jejunostomy tubes, or peripheral or total parenteral nutrition. In an exemplary embodiment, the compositions of the invention may be administered orally as a dietary supplement.

Compositions for oral administration generally contain inert excipients in addition to the amino acid ingredients of the composition. Oral preparations may be enclosed in gelatin capsules or compressed into tablets. Common excipients used in such preparations include pharmaceutically compatible fillers/diluents such as microcrystalline cellulose, hydroxypropyl methylcellulose, starch, lactose, sucrose, glucose, mannitol, sorbitol, dibasic calcium phosphate, or calcium carbonate; binding agents such as alginic acid, carboxymethylcellulose, microcrystalline cellulose, gelatin, gum tragacanth, or polyvinylpyrrolidone; disintegrating agents such as alginic acid, cellulose, starch, or polyvinylpyrrolidone; lubricants such as calcium stearate, magnesium stearate, talc, silica, or sodium stearyl fumarate; glidants such as colloidal silicon dioxide; sweetening agents such as sucrose or saccharin; flavoring agents such as peppermint, methyl salicylate, or citrus flavoring; coloring agents; and preservatives such as antioxidants (e.g., vitamin A, vitamin C, vitamin E, or retinyl palmitate), citric acid, or sodium citrate. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

The compositions according to the invention may be nutritionally complete, i.e. may include vitamins, minerals, trace elements as well as nitrogen, carbohydrate and fat and/or fatty acid sources so that they may be used as the sole source of nutrition supplying essentially all the required daily amounts of vitamins, minerals, carbohydrates, fat and/or fatty acids, proteins and the like.

(II) Methods

The present invention also provides methods for increasing muscle protein synthesis, prevention and/or treatment of a loss of any one of muscle mass, muscle strength, muscle function, and physical function, or any combination thereof. The method comprises administering to a subject a composition comprising a plurality of essential amino acids and optionally non-essential amino acids and/or nutrients. Suitable combinations and formulations for administration are described above in Section I and Section II, respectively.

The nutritional composition according to the disclsoure can advantageously be used for the manufacture of a medicament for the prevention or treatment of a disease or condition involving muscle decline in an a mammal, especially an adult mammal. Alternatively, the nutritional composition according to invention can advantageously be used for the manufacture of a medicament for the prevention or treatment of a disease or condition selected from the group of sarcopenia, muscle loss, insufficient muscle protein synthesis, muscle degradation, muscle proteolysis, muscle atrophy, muscle dystrophy, muscle catabolism, muscle wasting, loss of muscle strength, loss of muscle mass, loss of muscle function, loss of physical capacity, loss of physical performance, impaired mobility, frailty, surgery, disability, risk of falling and risk of fall-related fractures. Suitable subjects may include a human, a livestock animal, a companion animal, a laboratory animal, or a zoological animal. In a preferred embodiment, a subject is human. The magnitude of response may depend, in part, on the dose given, the exact combination of amino acids, the physiological condition and/or age of the subject, and/or the timing of administration in relation to performance of exercise.

Preferably, said subject is an elderly human. In this respect, it is submitted that in the context of this application, an elderly human is a person of the age of 50 years or more, in particular of the age of 55 or more, more in particular of the age of 60 or more, more in particular of the age of 65 or more. This rather broad definition takes into account the fact that the average age varies between different populations, on different continents, etc. Most developed world countries have accepted the chronological age of 65 years as a definition of 'elderly' or older person (associated with the age at which one may begin to receive pension benefits), but like many westernized concepts, this does not adapt well to e.g. the situation in Africa. At the moment, there is no United Nations (UN) standard numerical criterion, but the UN agreed cut-off is 60+ years to refer to the older population in Western world. The more traditional African definitions of an elder or 'elderly' person correlate with the chronological ages of 50 to 65 years, depending on the setting, the region and the country.

The nutritional composition according to the disclosure can advantageously be used for the prevention or treatment of muscle decline, in particular loss of muscle mass, during or following body weight maintenance, during or following energy restriction, during or following bed rest or during recovery following physical trauma. In a particularly preferred embodiment the compositions of the invention are used in the treatment of a subject, e.g. a subject suffering from overweight or obesity, said subject following a weight loss program, an energy restriction program and/or an exercise program. Said subject may be a child, an adolescent, an adult or an elderly subject. In an embodiment said subject is a child, an adolescent or an adult.

Muscle mass and function are progressively lost with aging, so that by age of 60 many otherwise healthy human subjects have reached a threshold where function begins to be affected. In an aspect, administering a composition of the invention to any healthy subject may increase muscle protein synthesis, increase muscle strength, increase muscle function, or a combination thereof, though the magnitude of the response may vary depending on age and/or the physiological condition of the subject.

The loss of body protein frequently accompanies illness, whether the illness is short term or long term. In another aspect, administering a combination of the invention to a subject that lost body protein as a result of illness may increase muscle protein synthesis, increase muscle strength, increase muscle function, or a combination thereof in the subject. In another aspect, administering a combination of the invention to a subject at risk of or experiencing muscle atrophy may increase muscle protein synthesis, increase muscle strength, increase muscle function, or a combination thereof. Non-limiting examples of subjects at risk of or experiencing muscle atrophy include humans with a sedentary lifestyle, people with seated jobs, medical conditions that limit movement, subjects that are bedridden, subjects who are away from Earth's gravity, subjects with an injury to a nerve that connects to muscle, and subjects at risk f or diagnosed with a disease affecting the nerves that control muscles. Non-limiting examples of diseases, disorders or conditions in which muscle atrophy occurs includes polio, Guillan-Barre syndrome, chronic obstructive pulmonary disease, congestive heart failure, acute coronary syndrome, chronic heart failure, cardiac cachexia, cancer, sarcopenia, spinal cord injury, osteoarthritis, arthritis, stroke, malnutrition, muscular dystrophy (e.g. Becker, congenital, Duchenne, Distal, Emery-Dreifuss, Facioscapulohumeral, Limb-Girdle, Oculopharyngeal), spinal muscular atrophy (e.g. ALS, motor neuron disease, infantile progressive spinal muscular atrophy, intermediate spinal muscular atrophy, juvenile spinal muscular atrophy, adult spinal muscular atrophy), inflammatory myopathies (e.g. dermatomyositis, polymyositis), diseases of the peripheral nerve (e.g. Carcot-Marie tooth disease, Dejerine-Sottas disease, Friedreich's ataxia), diseases of the neuromuscular junction (Myasthenia gravis, Lambert-Eaton syndrome), metabolic diseases of the muscle (acid maltase deficiency, carnitine deficiency, carnitine palm ityl transferase deficiency, Debrancer enzyme deficiency, Lactate dehydrogenase deficiency, Mitochondrial deaminase deficiency, Phophorylase deficiency, Phosphofructokinase deficiency, Phosphoglycerate kinase deficiency), other myopathies (central core disease, hyperthyroid myopathy, myotonia congenita, myotubular myopathy, paramytonia congenita, periodic paralysis-hypokalemic-hyperkalemic), or any other disease or condition that requires a subject to be immobilized or on bed rest, especially chronic heart failure and cardiac cachexia.

The method of the invention generally comprises administering the amino acid composition to a subject. Suitable subjects include animals such as mammals and humans. Non-limiting examples of suitable animals include companion animals such as cats, dogs, rodents, and horses; research animal such as mice, rats and other rodents; agricultural animals such as cows, cattle, pigs, goats, sheep, horses, deer, chickens and other fowl; zoo animals; and primates such as chimpanzees, monkeys, and gorillas. In a preferred embodiment, the subject is a human. In another preferred embodiment, the subject is a mammal.

The frequency of administration may be once, twice, three times or more daily, or once, twice, three times or more per week or per month, as needed as to produce the desired effect. The amount administered to the subject can and will vary depending upon the subject (e.g. age, weight, health status), and the particular mode of administration. Those skilled in the art will appreciate that dosages may also be determined with guidance from Goodman & Goldman's The Pharmacological Basis of Therapeutics, Tenth Edition (2001), Appendix II, pp. 475-493, and the Physicians' Desk Reference.

The human subject may be of any age. In some embodiments, the human subject may be about 30, 40, 45, 50, 55, 60, 65, 70, 75, 80, 85, 90, 95 years of age or older. In some preferred embodiments, the human subject is 40 years of age or older. In other preferred embodiments, the human subject is 45 years of age or older. In yet other preferred embodiments, the human subject is 50 years of age or older. In still other preferred embodiments, the human subject is 55 years of age or older. In other preferred embodiments, the human subject is 60 years of age or older. In yet other preferred embodiments, the human subject is 65 years of age or older. In still other preferred embodiments, the human subject is 70 years of age or older. In other preferred embodiments, the human subject is 75 years of age or older. In still other preferred embodiments, the human subject is 80 years of age or older. In yet other preferred embodiments, the human subject is 85 years of age or older. In still other preferred embodiments, the human subject is 90 years of age or older.

In some embodiments, the subject may be an alternative of the embodiments for subjects that lack daily exercise.

In other embodiments, the subject may be an alternative of the embodiments for subjects that lack the ability to efficiently stimulate muscle protein synthesis.

In other embodiments, the subject may be recovering from lack of physical exercise. During high-intensity muscular physical exercises, the rate of muscular work being performed may exceed the ability of the blood supply to deliver oxygen, creating a condition which induces reductive stress in muscle cells and may lead to muscle damage, impaired performance, predisposition to injury and a prolonged recovery period. Non-limiting examples of physical exercises that may lead to muscle damage, impaired performance, predisposition to injury and a prolonged recovery period may include flexibility exercises such as stretching, aerobic exercises such as cycling, swimming, walking, skipping rope, rowing, running, hiking or playing tennis, anaerobic exercises, such as weight training, functional training, eccentric training or sprinting, strength training, agility training, or eccentric training.

(a) Improvement in Muscle Protein Synthesis

The method of the invention improves muscle protein synthesis in a subject receiving the amino acid composition relative to in a subject that did not receive said amino acid composition.

An increase in muscle protein synthesis may be measured by any method known in the art. For example, rates of protein synthesis and breakdown in muscle and blood have been measured for many years using radioactively labeled amino acids or amino acids labeled with stable isotopes. See for example, Yale J Biol Med 1997; 70(1): 65-76, incorporated herein by reference. Measurement of 3-methylhistidine excretion in urine or arteriovenous difference in 3-methylhistidine is used as a measure of the unidirectional rate of muscle protein breakdown. Total body skeletal mass can be measured using dual-energy X-ray (DEXA) absorptiometry or by CT; see, for example, Am J Clin Nutr 2002; 76:378-83, and J Appl Physiol 1985 incorporated herein by reference. Methods for measuring muscle strength or function are also well known in the art. For example, change in muscle strength and function can be assessed using basic standardized tests as described in B J Nutr 2012; 108: S88-93 or in Lu et al. (2012) "Strength and Functional Measurement for Patients with Muscular Dystrophy" Muscular Dystrophy, Dr. Madhuri Hegde (Ed.), each hereby incorporated by reference.

In some embodiments, a method of the invention may increase muscle protein synthesis by at least 2-fold. For example, muscle protein synthesis may increase at least 2-fold, at least 3-fold, at least 4-fold, at least 5-fold, at least 6-fold, at least 7-fold, at least 8-fold, at least 9-fold, at least 10-fold or more following administration of a combination of the invention. In some embodiments, a method of the invention may increase muscle strength by at least 2-fold. For example, muscle strength may increase at least 2-fold, at least 3-fold, at least 4-fold, at least 5-fold, at least 6-fold, at least 7-fold, at least 8-fold, at least 9-fold, at least 10-fold or more following administration of a combination of the invention. In some embodiments, a method of the invention may increase muscle function by at least 2-fold. For example, muscle function synthesis may increase at least 2-fold, at least 3-fold, at least 4-fold, at least 5-fold, at least 6-fold, at least 7-fold, at least 8-fold, at least 9-fold, at least 10-fold or more following administration of a combination of the invention. In other embodiments, a method of the invention may increase muscle protein synthesis, muscle strength and muscle function, or a combination thereof. Methods for measuring muscle protein synthesis, muscle strength and muscle function are known in the art and further detailed in the Examples.

(III) Kits

Also provided are kits. Such kits can include a composition described herein and, in certain embodiments, instructions for administration. Such kits can facilitate performance of the methods described herein. When supplied as a kit, the different components of the composition can be packaged in separate containers and admixed immediately before use. Components include, but are not limited to an amino acid composition, as described herein. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Definitions

It is to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. The terms "comprising," "including," and "having" are intended to be inclusive and mean that there may be additional elements other than the listed elements. Further, all units, prefixes, and symbols may be denoted in its SI accepted form.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," 5th Ed., Smith, M. B. and March, J., eds. John Wiley & Sons, New York: 2001, the entire contents of which are hereby incorporated by reference.

The term "mmol", as used herein, is intended to mean millimole. The term "equiv", as used herein, is intended to mean equivalent. The term "mL", as used herein, is intended to mean milliliter. The term "g", as used herein, is intended to mean gram. The term "kg", as used herein, is intended to mean kilogram. The term "µg", as used herein, is intended to mean micrograms. The term "h", as used herein, is intended to mean hour. The term "min", as used herein, is intended to mean minute. The term "M", as used herein, is intended to mean molar. The term "µL", as used herein, is intended to mean microliter. The term "µM", as used herein, is intended to mean micromolar. The term "nM", as used herein, is intended to mean nanomolar. The term "N", as used herein, is intended to mean normal. The term "amu", as used herein, is intended to mean atomic mass unit. The term "° C.", as used herein, is intended to mean degree Celsius. The term "wt/wt", as used herein, is intended to mean weight/weight. The term "v/v", as used herein, is intended to mean volume/volume. The term "MS", as used herein, is intended to mean mass spectroscopy. The term "HPLC", as used herein, is intended to mean high performance liquid chromatograph. The term "RT", as used herein, is intended to mean room temperature. The term "e.g.", as used herein, is intended to mean example. The term "N/A", as used herein, is intended to mean not tested.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾. This applies regardless of the breadth of the range. In the context of this application, the term "at least" also includes the starting point of the open range. For example, an amount of "at least 95 weight %" means any amount equal to 95 weight % or above.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The term "about," as used herein, refers to variation in the numerical quantity that can occur, for example, through typical measuring techniques and equipment, with respect to any quantifiable variable, including, but not limited to, mass and volume. Further, given solid and liquid handling procedures used in the real world, there is certain inadvertent error and variation that is likely through differences in the manufacture, source, or purity of the ingredients used to make the compositions or carry out the methods and the like.

The methods and compositions of the present invention may comprise, consist essentially of, or consist of the components and ingredients of the present invention as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

As various changes could be made in the above-described compositions and methods without departing from the scope of the invention, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Experimental Evidence for an Effect of a 3.6 g Mixture of EAAs Plus Arginine The following study was performed to quantify the responses to two doses of the following amino acid formulation:
1-2% histidine
9-11% isoleucine
35-38% leucine
14-17% lysine
2-4% methionine
5-7% phenylalanine
8-9% threonine
9-11% valine
0.002-0.8% tryptophan
8-11% of arginine The acute stimulation of muscle protein synthesis resulting from the ingestion of either 3.6 or 10.8 g of the amino acid formulation described above was determined in a group of older subjects (see Table 1). The dose of 3.6 g was chosen because of the commercial viability of this dosage, based on both cost and taste. The response to 3.6 g was compared to a dosage of 10.8 g, since the higher dosage has been shown to not only stimulate muscle protein FSR, but to result in long-term outcome benefits in terms of strength and physical function (13). Muscle protein synthesis was determined before and after oral ingestion of the amino acid formulation.

TABLE 1

Subject Characteristics

|  | Male | Female | Total |
|---|---|---|---|
| Age (y) | 69 ± 3 | 68 ± 3 | 69 ± 2 |
| Sex | 6 | 6 | 12 |
| Body weight (kg) | 98.2 ± 5.3 | 71.7±6.3 | 83.7 ± 5.8 |
| Height (cm) | 183.8 ± 4.1 | 164.6 ± 1.7 | 173.3 ± 3.6 |
| BMI (kg/m$^2$) | 29.0 ± 1.2 | 26.3 ± 1.9 | 27.6 ± 1.2 |

Subjects were studied following an overnight fast. The study procedure involved a 5 hr. fasted period and a 3 hr. period after ingestion of the EAA formula. Subjects were given a constant infusion of tracer amounts of $^2H_5$-phenylalanine throughout the entire experiment. Muscle biopsies were taken after 2 and 5 hours of tracer infusion in the basal period, and at three hours after ingestion of the amino acid formula. Muscle free and protein bound phenylalanine enrichments were determined on each biopsy sample, and the fractional synthetic rate (FSR) of muscle protein calculated in the basal state and over the 3 hours after ingestion of the formula. Muscle protein FSR reflects the fraction of the total muscle that is produced in a unit of time (per hour in this experiment). Since in such a short period of time as this experiment there is no possibility that the amount of muscle protein changed from the beginning to the end of the study, muscle protein FSR is a direct reflection of the absolute rate of muscle protein synthesis. Values were calculated as the post value—pre value. In this way each subject served as their own control, as it has been shown in a variety of studies that the fasting muscle protein synthesis does not change in the time-frame of this study (eg, 14). The post ingestion value represents the integrated response of the entire 3 hours after ingestion of the formulation of amino acids.

Muscle FSR increased 0.0568%/h following ingestion of the 3.6 g dosage. This was a 57% increase above the basal FSR. The corresponding value was an increase of 0.0692%/h, which was a 76% increase over the basal value. Plasma EAA levels were also measured (Table 2).

TABLE 2

Amino Acid Concentrations (mol/L/3 hr)*

| Dose | EAAs | Leucine | Total BCAAs** |
|---|---|---|---|
| 3.6 g | 190 ± 23.2 | 42.6 ± 7.1 | 96.5 ± 11.3 |
| 10.8 G | 272.7 ± 34.6 | 82.9 ± 13.1 | 153.8 ± 22.8 |

*Increase over corresponding basal value, area under curve
**BCAAs are the branched chain amino acids leucine, valine, and isoleucine Although three times the amount of amino acids was given with the higher dosage, the increase in muscle protein FSR with the higher dosage was only marginally greater than in response to the 3.6 g dosage. Part of the explanation for the disproportionately greater response to the lower dosage is that the amino acid concentrations shown in Table 2 did not reflect the magnitude of the difference in the amount of amino acids ingested. This likely reflected an accelerated oxidation of the EAAs when provided at the higher dosage, and therefore less efficient utilization of the given dosage. Expressed differently, the signal at the muscle level to increase synthesis was disproportionately greater in response to the lower dose. It also indicates that the 3.6 g dosage was adequate to activate the synthetic response in muscle. Another likely explanation for the disproportionately large response to the 3.6 g dosage is that the amount of leucine in the 3.6 g formulation was sufficient to elicit a maximal activation of the initiation factors, and that the relatively small increase in FSR at the higher dose entirely reflected the increased provision of precursors for synthesis.

Newly synthesized protein contains all 20 amino acids, yet only 9 amino acids are contained in the formulation. The remainder of the amino acids are derived from the more efficient reutilization of amino acids derived from protein breakdown. Thus, some portion of amino acids including alanine, which is normally released from muscle as a primary means by which to transport nitrogen to the liver for incorporation into ammonia and urea for ultimate excretion in urine, are instead reutilized for protein synthesis. Consistent with this interpretation, it was observed in an earlier study that following ingestion of an EAA mixture, alanine concentration fell (15), reflecting enhanced reutilization for the process of protein synthesis. Consequently, in contrast to ingestion of amino acid mixtures that include alanine and other NEAAs there was no increase in urea production following EAA ingestion (15).

The results are unexpected due to the low dosage of this optimized ratio of EAA's plus arginine for stimulation of muscle protein synthesis. A Typical protein containing amino acids would require a dosage of well over 20 grams to have a much lower effect than 3.6 grams of this composition.

What is claimed is:

1. A method for stimulating muscle protein synthesis, the method comprising administering to a subject a composition comprising about 1 to 4 grams of the following concentrations of amino acids in terms of w/w %: about 1 to 2% of histidine, about 9 to 11% of isoleucine, about 35 to 38% of leucine, about 14 to 17% of lysine, about 2 to 4% of methionine, about 5 to 7% of phenylalanine, about 8 to 9% of threonine, about 9 to 11% of valine, about 0.005 to 0.8% of tryptophan, and about 8 to 11% of arginine, wherein stimulating muscle protein synthesis is increased approximately 50% compared to a subject not administered said amino acid composition.

2. The method of claim 1, wherein muscle protein synthesis is improved without physical exercise.

3. The method of claim 1, wherein the subject is a mammal.

4. The method of claim 1, wherein the subject is a human.

5. The method of claim 1, wherein the subject is a human 40 years of age or older.

6. The method of claim 1, wherein muscle protein synthesis improves approximately 50% with a minimum dose of 3.6 grams.

7. The method of claim 1, wherein the composition comprises the following concentrations of amino acids in terms of w/w %: 1.5% of histidine, 9.7% of isoleucine, 36.4% of leucine, 15.2% of lysine, 3% of methionine, 6.1% of phenylalanine, 8.5% of threonine, 10% of valine, 0.6% of tryptophan, and 9% of arginine.

8. The method of claim 6, wherein a 3.6 g dose of the composition is given to a human subject three times a day.

9. The method of claim 6, wherein a 3.6 g dose of the composition is given to a human subject one time a day.

10. The method of claim 6, wherein a 3.6 g dose of the composition is given to a human subject two times a day.

11. A composition comprising about 1 to 4 grams of the following amino acids: histidine, isoleucine, leucine, lysine, methionine, phenylalanine, threonine, valine, tryptophan, and arginine that stimulates muscle protein synthesis more than 50% with or without exercise.

12. A method for stimulating muscle protein synthesis using a dosage of about 1 to 4 grams, the method comprising administering to a subject a composition comprising the following concentrations of amino acids in terms of w/w %: about 1 to 2% of histidine, about 9 to 11% of isoleucine, about 35 to 38% of leucine, about 14 to 17% of lysine, about 2 to 4% of methionine, about 5 to 7% of phenylalanine, about 8 to 9% of threonine, about 9 to 11% of valine, about 0.005 to 0.8% of tryptophan, and about 8 to 11% of arginine, wherein stimulating muscle protein synthesis is increased relative to a subject not administered said amino acid composition.

13. The method of claim 12, wherein stimulating muscle protein synthesis is increased relative to a subject not administered said amino acid composition without exercise.

* * * * *